(12) United States Patent
Qin

(10) Patent No.: US 10,976,434 B2
(45) Date of Patent: Apr. 13, 2021

(54) ULTRASOUND DEVICES, ULTRASOUND METHODS, AND COMPUTER-READABLE MEDIA

(71) Applicant: THE HONG KONG POLYTECHNIC UNIVERSITY, Hong Kong (CN)

(72) Inventor: Jing Qin, Hong Kong (CN)

(73) Assignee: THE HONG KONG POLYTECHNIC UNIVERSITY, Hong Kong (CN)

( * ) Notice: Subject to any disclaimer, the term of this patent is extended or adjusted under 35 U.S.C. 154(b) by 430 days.

(21) Appl. No.: 16/112,855

(22) Filed: Aug. 27, 2018

(65) Prior Publication Data

US 2020/0064470 A1    Feb. 27, 2020

(51) Int. Cl.
*G01S 15/89*    (2006.01)
*G01S 7/52*    (2006.01)
*A61B 8/08*    (2006.01)

(52) U.S. Cl.
CPC ........ *G01S 15/8993* (2013.01); *A61B 8/0866* (2013.01); *A61B 8/483* (2013.01); *A61B 8/5269* (2013.01); *G01S 7/52053* (2013.01); *G01S 7/52077* (2013.01)

(58) Field of Classification Search
CPC ............. G01S 15/8993; G01S 7/52077; G01S 7/52053; G01S 15/8977; A61B 8/5269; A61B 8/483; A61B 8/0866; A61B 8/466
See application file for complete search history.

(56) References Cited

U.S. PATENT DOCUMENTS

2020/0064470 A1* 2/2020 Qin ..................... A61B 8/0866

FOREIGN PATENT DOCUMENTS

CN    109171815 A    * 1/2019

OTHER PUBLICATIONS

Jinta Zheng, et.al., "Towards Interactive and Realistic Rendering of 3D Fetal Ultrasound via Photon Mapping" IEEE International Symposium on Multimedia (2017), pp. 444-449.
Lei Zhu, et.al., "Feature-preserving ultrasound speckle reduction via L0 minimization" Neurocomputing 294 (2018), 48-60.

* cited by examiner

*Primary Examiner* — Daniel Pihulic
(74) *Attorney, Agent, or Firm* — Spruson & Ferguson (Hong Kong) Limited

(57) ABSTRACT

An ultrasound device, an ultrasound method, and computer-readable medium are provided. The ultrasound device includes: a sensor data receiver configured to receive ultrasound measurement data; a pre-processor configured to reduce noise of the ultrasound measurement data to obtain denoised data based on non-local self-similarity and phase information; a transfer function generator configured to generate a transfer function based on the denoised data; and a visualization circuit configured to generate a visualization of the ultrasound measurement data based on the transfer function and based on the denoised data.

19 Claims, 9 Drawing Sheets

ULTRASOUND DEVICES, ULTRASOUND METHODS, AND COMPUTER-READABLE MEDIA

TECHNICAL FIELD

The present invention generally relates to ultrasound devices, ultrasound methods, and computer-readable media, and more particularly relates to high-fidelity and real-time three-dimensional ultrasound visualization.

BACKGROUND OF THE DISCLOSURE

With the development of ultrasound imaging technology, 3D (three dimensional) ultrasound has become more and more popular in clinical practice. By integrating varying 2D (two-dimensional) images generated by reflected waves with different angles, volumetric ultrasound data, i.e. 3D ultrasound data, may be acquired. Compared with 2D ultrasound data, 3D ultrasound data can provide more anatomical information for more precise diagnosis and treatment.

One of the most important applications of 3D or 4D (four-dimensional, i.e. involving a time series of 3D data) ultrasound is fetal examination. It has been evidenced that 3D ultrasound can enhance detection accuracy of congenital defects.

Compared to its 2D counterpart, 3D ultrasound is especially helpful for assisting obstetricians to precisely evaluate the severity of abnormalities and take necessary actions to cope with them because 3D ultrasound is capable of displaying the abnormalities from different angles, and hence providing more diagnostic information.

However, nowadays, it is still challenging to visualize 3D fetal ultrasound data offering high-fidelity details in a real-time manner due to speckle noise, low signal-to-noise ratio and the complicated anatomical environment involving different tissues and organs in many cases. Existing visualization systems are incompetent at detail-aware visualization for precise diagnosis and treatment.

Thus, there is a need for a high-fidelity and real-time 3D (fetal) ultrasound visualization system. Furthermore, other desirable features and characteristics will become apparent from the subsequent detailed description and the appended claims, taken in conjunction with the accompanying drawings and this background of the disclosure.

SUMMARY

According to at least one embodiment of the present invention, an ultrasound device is provided. The ultrasound device includes: a sensor data receiver configured to receive ultrasound measurement data; a pre-processor configured to reduce noise of the ultrasound measurement data to obtain denoised data based on non-local self-similarity and phase information; a transfer function generator configured to generate a transfer function based on the denoised data; and a visualization circuit configured to generate a visualization of the ultrasound measurement data based on the transfer function and based on the denoised data.

According to at least one embodiment of the present invention, an ultrasound method is provided. The ultrasound method includes: receiving ultrasound measurement data; reducing noise of the ultrasound measurement data to obtain denoised data based on non-local self-similarity and phase information; generating a transfer function based on the denoised data; and generating a visualization of the ultrasound measurement data based on the transfer function and based on the denoised data.

According to at least one embodiment of the present invention, a non-transitory computer readable medium is provided. The non-transitory computer readable medium has stored thereon executable instructions to have an ultrasound device perform an ultrasound method. The ultrasound method includes: receiving ultrasound measurement data; reducing noise of the ultrasound measurement data to obtain denoised data based on non-local self-similarity and phase information; generating a transfer function based on the denoised data; and generating a visualization of the ultrasound measurement data based on the transfer function and based on the denoised data.

BRIEF DESCRIPTION OF THE DRAWINGS

The accompanying figures, where like reference numerals refer to identical or functionally similar elements throughout the separate views and which together with the detailed description below are incorporated in and form part of the specification, serve to illustrate various embodiments and to explain various principles and advantages in accordance with a present embodiment.

Skilled artisans will appreciate that elements in the figures are illustrated for simplicity and clarity and have not necessarily been depicted to scale.

DETAILED DESCRIPTION

The following detailed description is merely exemplary in nature and is not intended to limit the invention or the application and uses of the invention. Furthermore, there is no intention to be bound by any theory presented in the preceding background of the invention or the following detailed description. It is the intent of the present embodiment to present a high-fidelity and real-time 3D ultrasound visualization system, for example a high-fidelity and real-time 3D fetal ultrasound visualization system. Advantageously, the performance of current systems is improved by one or more of the following aspects. First, an effective speckle reduction is provided, so that, while reducing speckle noise, important anatomical features can be well preserved. Second, transfer functions are determined to clearly differentiate various organs or tissues in complex anatomical environment. Third, illumination models are provided to preserve more details while realistically displaying the geometric relationship among different organs and tissues in the visualization results.

Figure 1:
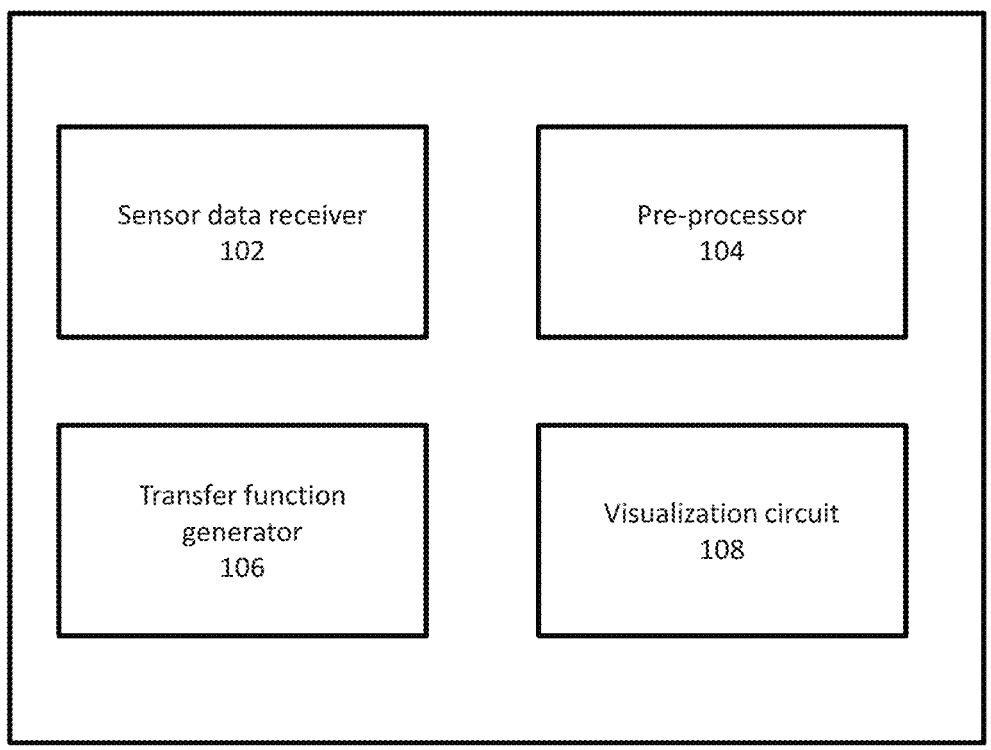
FIG. 1 depicts an ultrasound device according to various embodiments.

FIG. 1 depicts an ultrasound device 100 according to various embodiments. The ultrasound device 100 includes a sensor data receiver 102 (in other words: sensor data receiving module or sensor data receiving circuit) configured to receive ultrasound measurement data. In an embodiment, the sensor data receiver 102 may receive the ultrasound measurement data directly from an ultrasound sensor. In an alternative embodiment, the sensor data receiver 102 may receive the ultrasound measurement data from a storage device (not shown in FIG. 1); for example, the ultrasound measurement data may have been acquired from an ultrasound sensor and then been stored on the storage device.

The ultrasound device 100 further includes a pre-processor 104 (in other words: pre-processing module or pre-processing circuit) configured to reduce noise of the ultrasound measurement data to obtain denoised data. The pre-processor 104 may obtain the denoised data based on non-local self-similarity and phase information (in other words: based on a similarity of patches, wherein the patches are determined based on phase information). High-dimensional ultrasound visualization inevitably receives negative influence from the inherent speckle noise. In this regard, according to various embodiments, the pre-processor 104 removes speckle noise from the ultrasound measurement data before visualization.

In a present embodiment, the pre-processor 104 may carry out three main steps for the denoising. First, the pre-processor 104 integrates phase information of the ultrasound measurement data into a region covariance descriptor to estimate patch similarities in the ultrasound measurement data in order to further enhance its capability of discriminating features and speckle noise.

Given an input image S, the phase information is the feature asymmetry (FA) of the below equation, and the definition of FA is given by:

$$\begin{cases} FA = \dfrac{\lfloor |R_o| - |R_e| - \Theta \rfloor}{\sqrt[2]{R_o^2 + R_e^2} + \gamma} \\ R_o = f * S, R_o = (f * z_1 * S, f * z_2 * S), \end{cases}$$

where $\Theta$ describes the estimated noise threshold; $\lfloor . \rfloor$ is the zeroing operation of negative values; $\gamma$ is a constant to avoid division by zero; $z_1$ and $z_2$ are the Riesz filters, and f is the 2D isotropic Cauchy filter.

After obtaining the phase information (FA in the equation above), the phase information may be incorporated it into the computation of the region covariance descriptor for each patch. For the patch R (size: d×d), the phase based region covariance descriptor ($C_t$) is defined as:

$$C_R = \dfrac{1}{d^2 - 1} \sum_{i=0}^{d^2} (F_i - \mu)(F_i - \mu)^T$$

where $F_i$=(FA(p,q),S(p,q), $$\left|\dfrac{\partial S}{\partial x}\right|, \left|\dfrac{\partial S}{\partial y}\right|, \left|\dfrac{\partial^2 S}{\partial x^2}\right|, \left|\dfrac{\partial^2 S}{\partial y^2}\right|,$$

p,q) is the feature vector of the i-th pixel in R, and $\mu$ the mean feature vector of all pixels in the patch R.

In the definition of the $F_i$=(FA(p,q), S(p,q), $$\left|\dfrac{\partial S}{\partial x}\right|, \left|\dfrac{\partial S}{\partial y}\right|, \left|\dfrac{\partial^2 S}{\partial x^2}\right|, \left|\dfrac{\partial^2 S}{\partial y^2}\right|,$$

p,q), (p, q) is the spatial location of the pixel i; S(p, q) is the intensity value at the (p, q) of the input image S; FA(p, q) is the value at the (p, q) of the FA map; and $$\left|\dfrac{\partial S}{\partial x}\right|, \left|\dfrac{\partial S}{\partial y}\right|, \left|\dfrac{\partial^2 S}{\partial x^2}\right|, \left|\dfrac{\partial^2 S}{\partial y^2}\right|$$

are the 1st and 2nd derivatives on the input image S.

By integrating the phase information into the region covariance descriptor, advantageously, the geometry and frequency information of a local patch may be encoded via second-order statistical relations and several simple features.

As shown in the definition of the $C_R$ above, $C_R$ is the average of the region covariance of all the pixels in the region R, and the region covariance at each pixel involves a covariance matrix operation. Since the covariance matrix is a second-order statistical operator, we claimed that the $C_R$ can describe the second-order statistical relations.

According to the definition of the feature vector $F_i$=(FA (p,q), S(p,q), $$\left|\dfrac{\partial S}{\partial x}\right|, \left|\dfrac{\partial S}{\partial y}\right|, \left|\dfrac{\partial^2 S}{\partial x^2}\right|, \left|\dfrac{\partial^2 S}{\partial y^2}\right|,$$

p,q), the simple features are all the elements of $F_i$ excluding the FA(p,q), and thus they are S(p,q), $$\left|\dfrac{\partial S}{\partial x}\right|, \left|\dfrac{\partial S}{\partial y}\right|, \left|\dfrac{\partial^2 S}{\partial x^2}\right|, \left|\dfrac{\partial^2 S}{\partial y^2}\right|,$$

p, and q.

Hence, different patches can be effectively separated because phase information can better discriminate features and speckle noise (compared to, for example, intensity and gradient information). Thus, advantageously, important features may be preserved when removing the speckle noise.

Given an input image S, we can obtain a patch for each pixel of S. For a given pixel j, the patch of the pixel j is defined as the square region centered at the pixel j, and the size of the square region is d×d. d may empirically be set as 7.

According to various embodiments, it may be desired to perform the low-rank recovery for each pixel of the input image by finding a set of similar patches. Given a pixel k, we first obtain the patch centered at k, and this patch is the 'reference patch', and then we can find a set of similar patches of the 'reference patch.

Second, once a set of most similar patches for each reference patch has been identified, the pre-processor 104 forms a patch group (PG) matrix by stacking each similar patch (for each reference patch) as one column (this may be referred to as patch group (PG) matrix formulation). For a despeckled image, its PG matrix should have a low-rank property due to high similarities between those patches, while the PG matrix rank of a noisy input image shall be relatively large due to the corruption of the speckle noise. In this regard, the despeckling problem may be transferred to a problem of low-rank matrix recovery with noisy elements. This new formulation advantageously enables an elegant combination of the NSS and phase information for speckle reduction. Advantageously, features may be better preserved, and speckle noise may at the same time be efficiently removed.

Third, the pre-processor 104 estimates the despeckled PG matrix (in other words: denoised matrix) by the low rank approximation in the singular value decomposition domain. This involves various matrix calculations, and thus, it may be carried out by graphic processing units (GPUs). According to various embodiments, the pre-processor 104 includes one or more GPUs. According to various embodiments, the pre-processor 104 is a GPU. The pre-processor 104 may carry out the denoising in a real-time manner for a 3D ultrasound with normal resolution. Based on the denoised matrix, the denoised data may be obtained.

The ultrasound device 100 further includes a transfer function generator 106 (in other words: transfer function generation module or transfer function generation circuit) configured to generate a transfer function based on the denoised data (i.e. the data that has been generated by the pre-processor 104). In volume visualization domain, transfer functions are responsible for allocating opacity and color values to voxels in the volumetric dataset. These transfer functions may be critical to the quality of visualization results. Traditional transfer functions, which may achieve reasonable results on CT (computer tomography) or MRI (magnetic resonance imaging) datasets, failed to obtain satisfactory results on ultrasound dataset due to low signal-to-noise ratio and severely blurred boundaries. According to various embodiments, the transfer function generator 106 may perform a clustering-based automated transfer function generation, based on the affinity propagation (AP) clustering method of Frey and Dueck. The clustering method may have fast convergence speed and accurate clustering performance.

According to various embodiments, to obtain meaningful clustering results, two similarity measurements may be introduced: intensity-gradient magnitude similarity and spatial similarity.

For intensity-gradient magnitude (IGM) similarity, close bins in the IGM histogram may have similar intensity and gradient magnitude. In this regard, Euclidean distance may be employed to measure the IGM similarity of two bins.

For spatial similarity, the similarity may be evaluated between two bins using the number of direct neighborhood relations between the two bins.

These two similarity measurements can accurately and effectively bring the voxels of the same tissue together and differentiate the voxels of different tissues so that the generated transfer functions (TFs) can assign different optical properties to different tissues. The transfer function generator 106 may first perform AP clustering based on the peaks in the intensity-gradient histogram and the measurements of spatial correlation. Then, based on the initialization of the transfer function, the transfer function generator 106 may determine the distribution of the visibility of these clusters with each cluster representing a kind of tissue. An energy function may be defined to measure the difference of the current distribution and target visibility distribution, and the gradient descent method may be used to solve (in other words: minimize) this energy function.

Advantageously, by carrying out the automated transfer function design scheme based on the affinity propagation (AP) clustering method, the main characteristics of the ultrasound volumes can clearly and effectively be presented.

The ultrasound device 100 further includes a visualization circuit 108 (in other words: a visualization module) configured to generate a visualization of the ultrasound measurement data based on the transfer function (determined by the transfer function generator 106) and based on the denoised data (determined by the pre-processor 104). The visualization circuit 108 may employ a global illumination model based on volumetric photon mapping. For example, the volumetric photon mapping (VPM) of Zhang, Dong, and Ma may be used, which can simulate light transportation including both absorption and scattering.

According to various embodiments, the visualization circuit 108 may carry out a real-time version of VPM by carrying out various techniques and leveraging GPU acceleration, like will be described in the following.

According to various embodiments, a GPU-accelerated volumetric photon mapping (VPM) method may be a bi-directional path tracing method combined with a density estimation that samples eye and light paths (photons), whereby the eye paths are kept short to avoid the expensive final gathering. There are no sampled indirect eye paths that are saved for deterministic reflections.

In the standard VPM method, the first step is to generate photons for each basis light. In order to avoid wasting photons, according to various embodiments, photons may be cast at the boundary voxels of the volume. Millions of photons may be emitted first. According to the single instruction of the multi-thread programming model of CUDA, a GPU thread may be built for each emitted photon for tracking purposes. This method may be easy to implement, but the threads are not one-time completions. Instead, these threads are batch-executed and internally scheduled according to the GPU rule because the number of threads that can be concurrently executed in a GPU is limited. The equal distribution method may be generally used for the emitted photons. Although this method has good independent concurrency, the time needed to track each photon, and the emission of the same number of photons varies because the photon reflection and the refraction tracking route for each photon are different. Therefore, some thread resources will be wasted, which prolongs the emission process.

The method should avoid resource wasting to improve emission efficiency due to real-time inter-operability requirements. Therefore, according to various embodiments, a method may be provided wherein all threads co-complete the photon emission tasks. A variable named Count has been established to represent the number of photons that all threads have emitted, and initialized its value to 0. When a thread emits a photon, Count is increased by 1 unit until it reaches the total number of photons to be emitted during the entire emission process. This reduces the thread idle time and improves the emission efficiency.

After photons are shot, it may be desired to track each of them, and record their behaviors in the scene. There are three possibilities for the photon when it collides with a surface object: the photon is reflected, absorbed, or transmitted through. Traditional VPM uses K-D tree data structures to store the photons, which need large storage space, and the final gathering thus becomes time-consuming. In order to reduce these artifacts, according to various embodiments, a volume texture is used to store photons in our implementation.

After photons are traced and stored, an indirect illumination volume is obtained that is needed to be rendered using the ray-casting method. The traditional photon mapping technique uses ray-marching for rendering, which is unsuitable for ultrasonic data, since the volume is too small to sample. According to various embodiments, volume texture is used to store the photons, and a new destiny estimation method is applied to quickly obtain the indirect illumination radiance.

The visualization circuit 108 may employ a (volume) rendering scheme, in which the VPM and direct illumination are seamlessly combined together to figure out the scattering effects. New features of GPUs buffers are used, and a new estimation model may be provided to more accurately evaluate the photon's positions and energies.

In principle, photon mapping can also be considered as a destiny estimation problem. The samples of the irradiance can be represented as the number of photon hits. According to various embodiments, the calculation of multiple scattering radiance in the volume space of the screen space may be employed (shown in FIG. 7C) since the step of sampling in the ray-casting is small, and the photon can also be seen sequentially. Instead of splatting photons on the screen, according to various embodiments, rays may be cast from the image screen to the indirect illumination volume and subsequently sampled the photons. Since the effect of indirect lighting in dense media is the outcome of the diffusion of light, the light travels more distance in the volume than it would if only direct attenuation is considered. Translucency implies blurring of the light as it travels through the medium due to scattering effects. The destiny estimation is computed in the 2D image space using the Gaussian blur.

With the advanced global illumination model and volumetric photon mapping, realistic and real-time 3D ultrasound visualization may be provided.

With the VPM according to various embodiments, advantageously, more depth information and details than commonly used, local illumination models may be provided.

Figure 2:
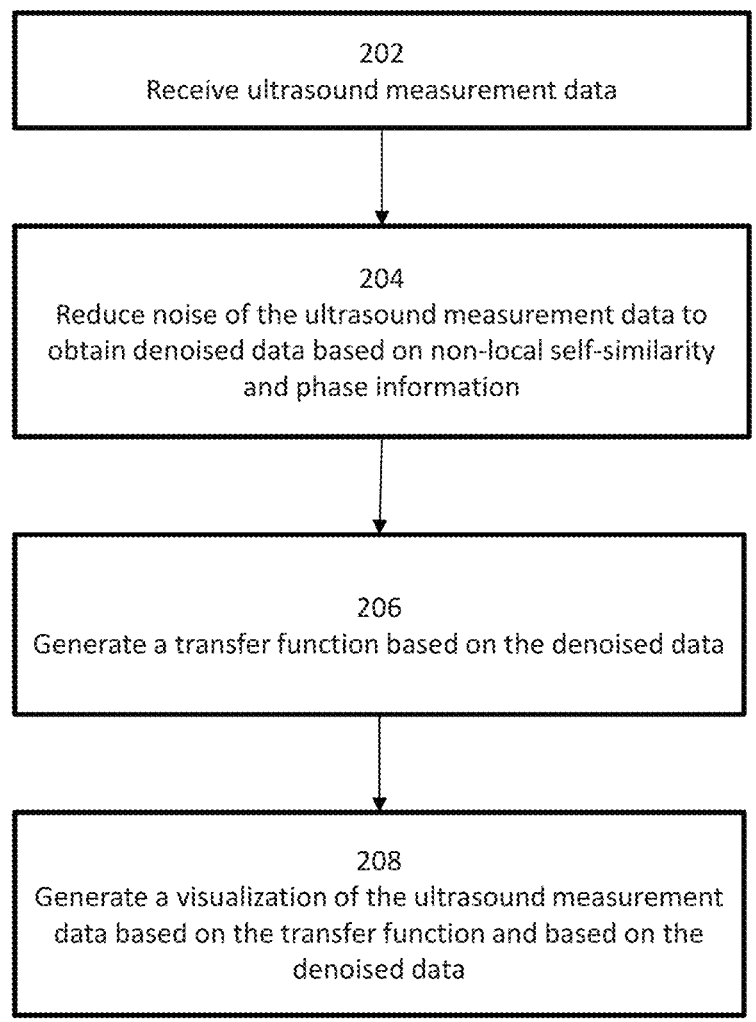
FIG. 2 depicts a flow diagram illustrating an ultrasound method according to various embodiments.

FIG. 2 shows a flow diagram 200 illustrating an ultrasound method according to various embodiments. At 202, ultrasound measurement data may be received. At 204, noise of the ultrasound measurement data may be reduced (to obtain denoised data) based on non-local self-similarity and phase information. At 206, a transfer function may be generated based on the denoised data. At 208, a visualization of the ultrasound measurement data may be generated based on the transfer function and based on the denoised data.

Reducing noise of the ultrasound measurement data based on non-local self-similarity and phase information (step 204) may include estimating patch similarities of the ultrasound measurement data. The patch similarities may be estimated based on integrating phase information of the ultrasound measurement data into a region covariance descriptor.

According to various embodiments, a patch group matrix may be determined based on the patch similarities. A denoised matrix of lower rank corresponding to the patch group matrix may be determined, for example based on a singular value decomposition of the patch group matrix.

According to various embodiments, generating the visualization may include using the transfer function to differentiate in the ultrasound measurement data between organs and tissues. The transfer function may be determined based on clustering of voxels obtained based on the ultrasound measurement data. According to various embodiments, the visualization may be generated based on volumetric photon mapping.

According to various embodiments, a non-transitory computer readable medium may be provided. The non-transitory computer readable medium may have stored thereon executable instructions to have an ultrasound device (for example the ultrasound device shown in FIG. 1) perform an ultrasound method (for example the ultrasound method illustrated in FIG. 2).

Figure 3:
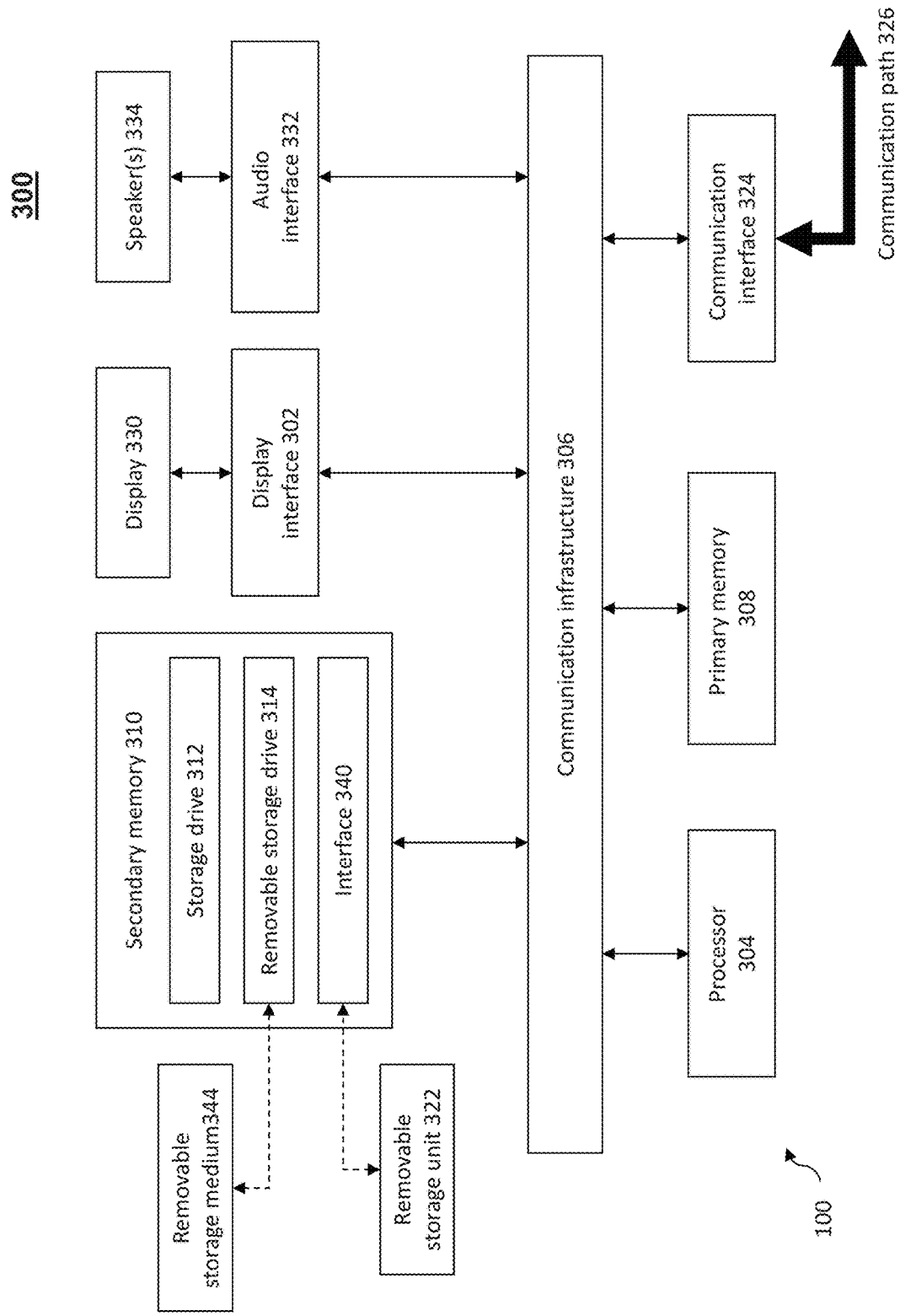
FIG. 3 depicts an exemplary computing device according to various embodiments.

FIG. 3 depicts an exemplary computing device 300, hereinafter interchangeably referred to as a computer system 300 or as a device 300, where one or more such computing devices 300 may be used to implement the ultrasound device 100 shown in FIG. 1. The following description of the computing device 300 is provided by way of example only and is not intended to be limiting.

As shown in FIG. 3, the example computing device 300 includes a processor 304 for executing software routines. Although a single processor is shown for the sake of clarity, the computing device 300 may also include a multi-processor system. The processor 304 is connected to a communication infrastructure 306 for communication with other components of the computing device 300. The communication infrastructure 306 may include, for example, a communications bus, cross-bar, or network.

The computing device 300 further includes a primary memory 308, such as a random access memory (RAM), and a secondary memory 310. The secondary memory 310 may include, for example, a storage drive 312, which may be a hard disk drive, a solid state drive or a hybrid drive and/or a removable storage drive 314, which may include a magnetic tape drive, an optical disk drive, a solid state storage drive (such as a USB flash drive, a flash memory device, a solid state drive or a memory card), or the like. The removable storage drive 314 reads from and/or writes to a removable storage medium 344 in a well-known manner. The removable storage medium 344 may include magnetic tape, optical disk, non-volatile memory storage medium, or the like, which is read by and written to by removable storage drive 314. As will be appreciated by persons skilled in the relevant art(s), the removable storage medium 344 includes a computer readable storage medium having stored therein computer executable program code instructions and/or data (for example for performing the ultrasound method illustrated by the flow diagram 200 of FIG. 2).

In an alternative implementation, the secondary memory 310 may additionally or alternatively include other similar means for allowing computer programs or other instructions to be loaded into the computing device 300. Such means can include, for example, a removable storage unit 322 and an interface 350. Examples of a removable storage unit 322 and interface 350 include a program cartridge and cartridge interface (such as that found in video game console devices), a removable memory chip (such as an EPROM or PROM) and associated socket, a removable solid state storage drive (such as a USB flash drive, a flash memory device, a solid state drive or a memory card), and other removable storage units 322 and interfaces 350 which allow software and data to be transferred from the removable storage unit 322 to the computer system 300.

The computing device 300 also includes at least one communication interface 324. The communication interface 324 allows software and data to be transferred between computing device 300 and external devices via a communication path 326. In various embodiments of the inventions, the communication interface 324 permits data to be transferred between the computing device 300 and a data communication network, such as a public data or private data communication network. The communication interface 324 may be used to exchange data between different computing devices 300 which such computing devices 300 form part an interconnected computer network. Examples of a communication interface 324 can include a modem, a network interface (such as an Ethernet card), a communication port (such as a serial, parallel, printer, GPIB, IEEE 1394, RJ45, USB), an antenna with associated circuitry and the like. The communication interface 324 may be wired or may be wireless. Software and data transferred via the communication interface 324 are in the form of signals which can be electronic, electromagnetic, optical or other signals capable of being received by communication interface 324. These signals are provided to the communication interface via the communication path 326.

As shown in FIG. 3, the computing device 300 further includes a display interface 302 which performs operations for rendering images to an associated display 330 and an audio interface 332 for performing operations for playing audio content via associated speaker(s) 334. For example, the display 330 may display the visualization generated at step 208 illustrated in FIG. 2.

As used herein, the term "computer program product" (or computer readable medium, which may be a non-transitory computer readable medium) may refer, in part, to removable storage medium 344, removable storage unit 322, a hard disk installed in storage drive 312, or a carrier wave carrying software over communication path 326 (wireless link or cable) to communication interface 324. Computer readable storage media (or computer readable media) refers to any non-transitory, non-volatile tangible storage medium that provides recorded instructions and/or data to the computing device 300 for execution and/or processing. Examples of such storage media include magnetic tape, CD-ROM, DVD, Blu-Ray™ Disc, a hard disk drive, a ROM or integrated circuit, a solid state storage drive (such as a USB flash drive, a flash memory device, a solid state drive or a memory card), a hybrid drive, a magneto-optical disk, or a computer readable card such as a PCMCIA card and the like, whether or not such devices are internal or external of the computing device 300. Examples of transitory or non-tangible computer readable transmission media that may also participate in the provision of software, application programs, instructions and/or data to the computing device 600 include radio or infra-red transmission channels as well as a network connection to another computer or networked device, and the Internet or Intranets including e-mail transmissions and information recorded on Websites and the like.

The computer programs (also called computer program code) are stored in main memory 308 and/or secondary memory 310. Computer programs can also be received via the communication interface 324. Such computer programs, when executed, enable the computing device 300 to perform one or more features of embodiments discussed herein. In various embodiments, the computer programs, when executed, enable the processor 304 to perform features of the above-described embodiments. Accordingly, such computer programs represent controllers of the computer system 300.

Software may be stored in a computer program product and loaded into the computing device 300 using the removable storage drive 314, the storage drive 312, or the interface 340. The computer program product may be a non-transitory computer readable medium. Alternatively, the computer program product may be downloaded to the computer system 300 over the communications path 326. The software, when executed by the processor 304, causes the computing device 300 to perform functions of embodiments described herein.

It is to be understood that the embodiment of FIG. 3 is presented merely by way of example. Therefore, in some embodiments one or more features of the computing device 300 may be omitted. Also, in some embodiments, one or more features of the computing device 300 may be combined together. Additionally, in some embodiments, one or more features of the computing device 300 may be split into one or more component parts. The main memory 308 and/or the secondary memory 310 may serve(s) as the memory for the ultrasound device 100; while the processor 304 may serve as the processor of the ultrasound device 200.

Figure 4:
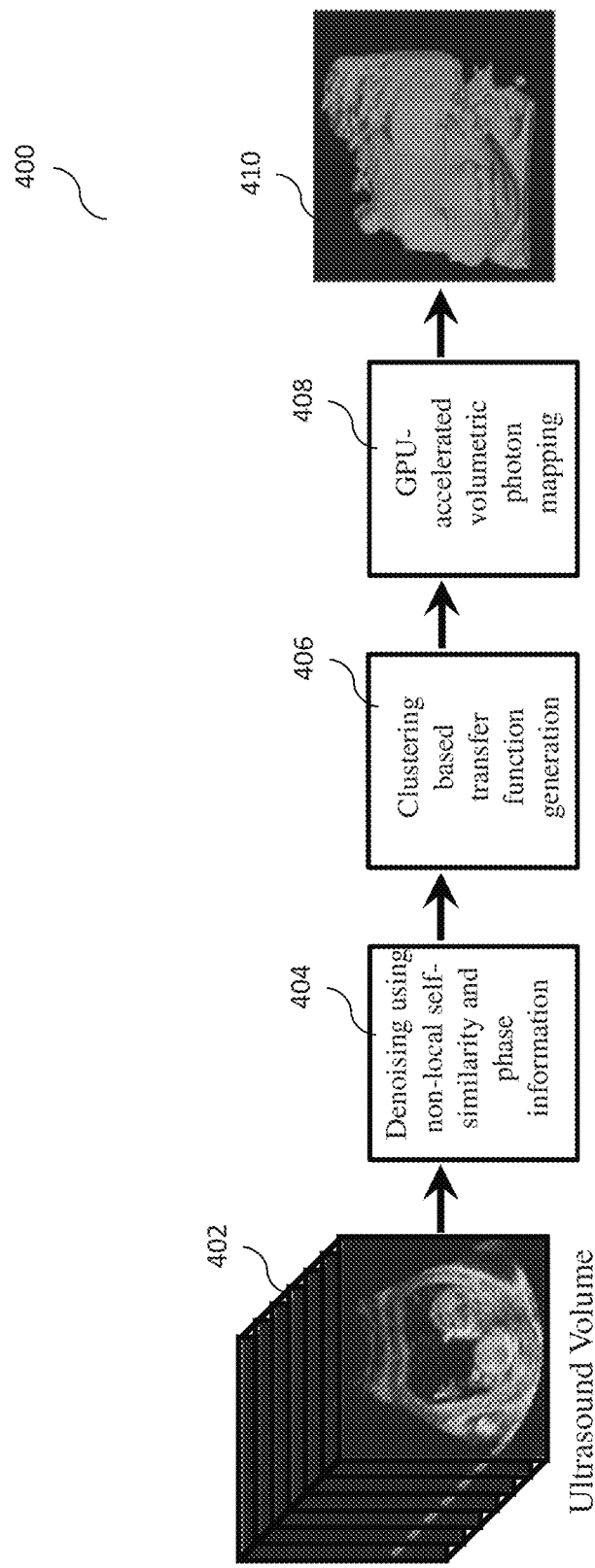
FIG. 4 depicts a flow diagram illustrating use of the ultrasound visualization system according to various embodiments.

FIG. 4 depicts a flow diagram 400 illustrating use of the ultrasound visualization system according to various embodiments. Starting from an ultrasound volume 402 (which for example may include several ultrasound images, for example stacked, for example of different planes), in step 404, denoising using non-local self-similarity and phase information may be carried out. In step 406, clustering based transfer function generation may be may be performed. In step 408, GPU-accelerated volumetric photon mapping may be carried out to arrive at a 3D visualization 410.

Figure 5:
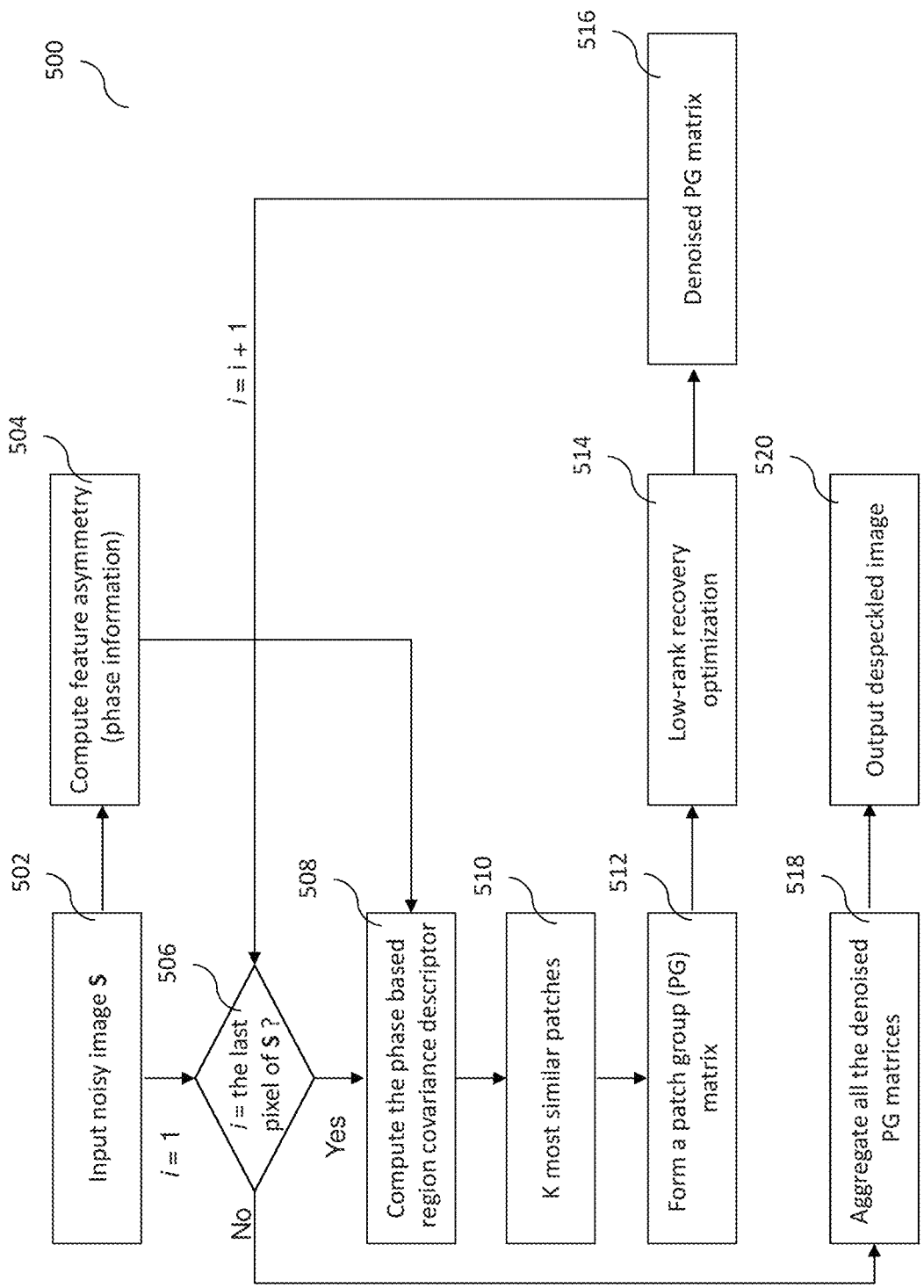
FIG. 5 depicts a flow diagram illustrating a denoising method based on non-local self-similarity and phase information according to various embodiments.

FIG. 5 depicts a flow diagram 500 illustrating a denoising method based on non-local self-similarity and phase information according to various embodiments. Starting from a noisy input image S (502) and with integer counter i set to 1, feature asymmetry (phase information) is determined in step 504, and at step 506, it is determined whether i is equal to the last pixel of S. If it is determined at step 506 that i is equal to the last pixel of S, processing may continue at step 508. If it is determined at step 506 that i is not equal to the last pixel of S, processing may continue at step 518. At step 508, the phase based region covariance description may be determined. At step 510, an integer number K of most similar patches may be determined. At step 512, a patch group (PG) matrix may be formed. At step 514, low-rank recovery optimization may be performed, in order to obtain a denoised PG matrix at step 516. After step 516, i may be incremented by 1, and processing may proceed at step 506. At step 518, all the denoised PG matrices may be aggregated, and at step 520, a despeckled image may be output.

Figure 6:
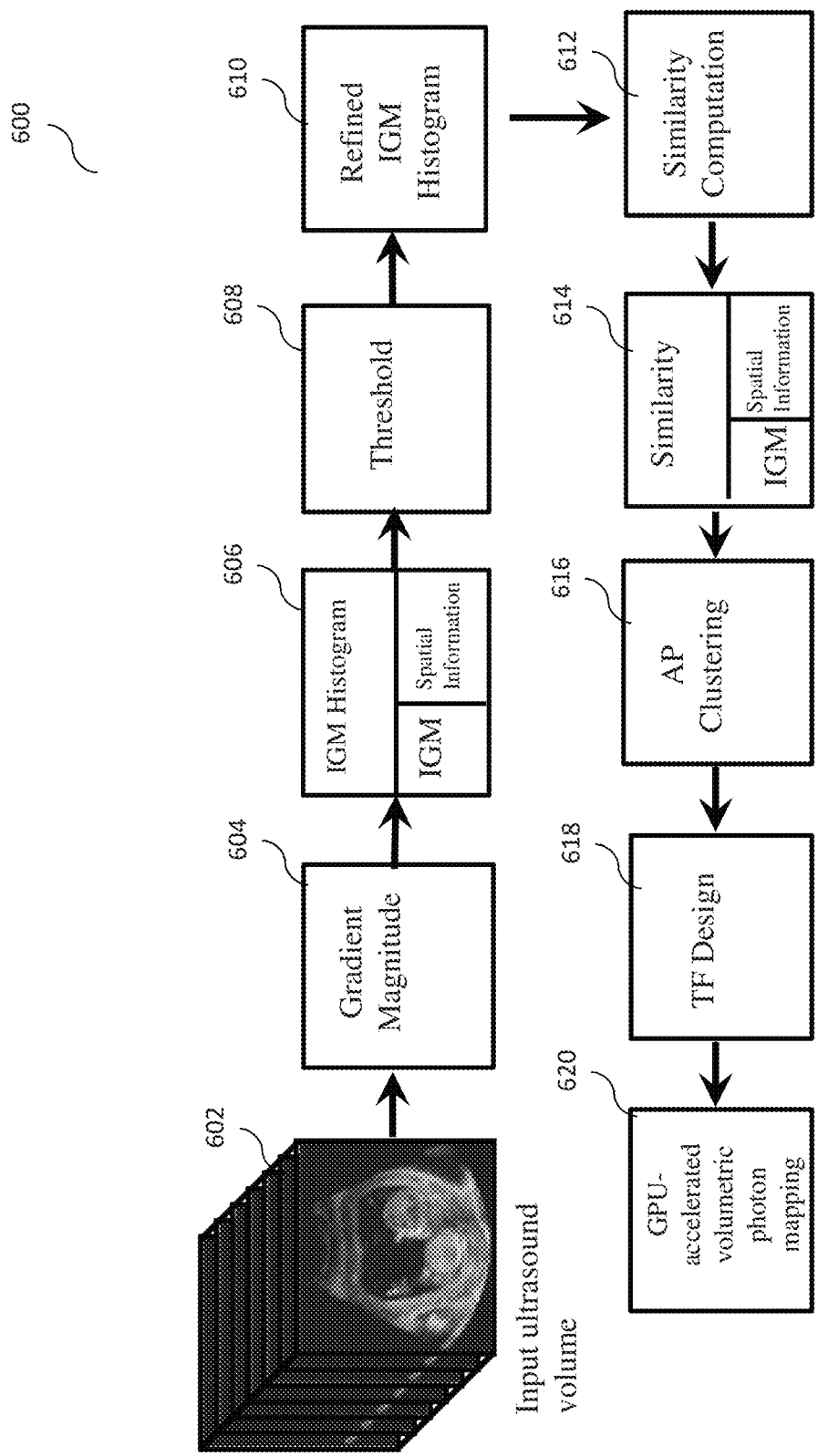
FIG. 6 depicts a flow diagram illustrating a clustering-based automated transfer function generation method according to various embodiments.

FIG. 6 depicts a flow diagram 600 illustrating a clustering-based automated transfer function generation method according to various embodiments. Starting from an input ultrasound volume 602, a gradient magnitude may be determined at step 604. At step 606, IGM, IGM histogram, and spatial information may be determined. At step 608, a threshold may be applied, in order to obtain a refined IGM histogram at step 610. Similarity computation may be performed at step 612. Similarity information, IGM, and spatial information may be carried out at step 614. AP clustering may be performed at step 616. TF (transfer function) design may be carried out at step 618. At step 620, GPU-accelerated volumetric photon mapping may be carried out.

Figure 7A:
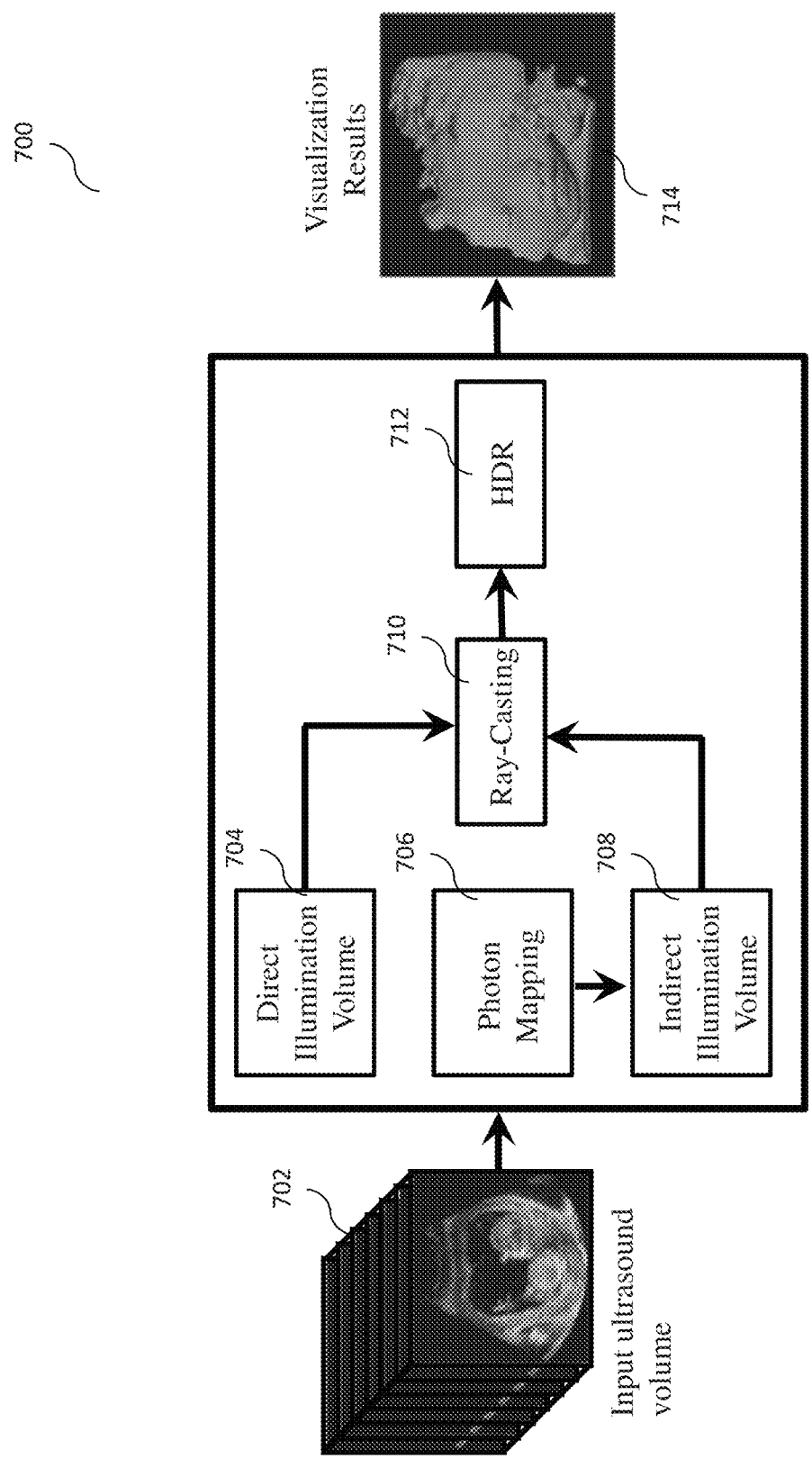
FIG. 7A depicts a workflow of the GPU-accelerated volumetric photon mapping method according to various embodiments.

FIG. 7A depicts a workflow 700 of the GPU-accelerated volumetric photon mapping method according to various embodiments. Processing may start from an input ultrasound volume 702. At step 704, a direct illumination volume may be determined. Photon mapping may be performed at step 706, and an indirect illumination volume may be determined at step 708. Ray-casting may be carried out at step 710, for example based on the direct illumination volume and the indirect illumination volume. At step 712, an HDR (high-dynamic range) method may be carried out. The limited range of the ultrasound display is inadequate to present results of high precision volume rendering. Thus, this post-processing step 712 may be added to solve this problem using a high-dynamic range (HDR) method that are routinely used in digital photography, to adjust images with an extensive range of intensities. HDR methods allow users to work with images with greater dynamic ranges of the luminance compared to the standard, low-dynamic-range (LDR) digital imaging techniques. According to various embodiments, a tone-mapping technique may be applied which is an HDR method that maps the high range of luminance images to standard devices with lower dynamic ranges. Advantageously, the local contrast between the features can be well preserved by applying the HDR method. A visualization result 714 may be obtained.

Figure 7B:
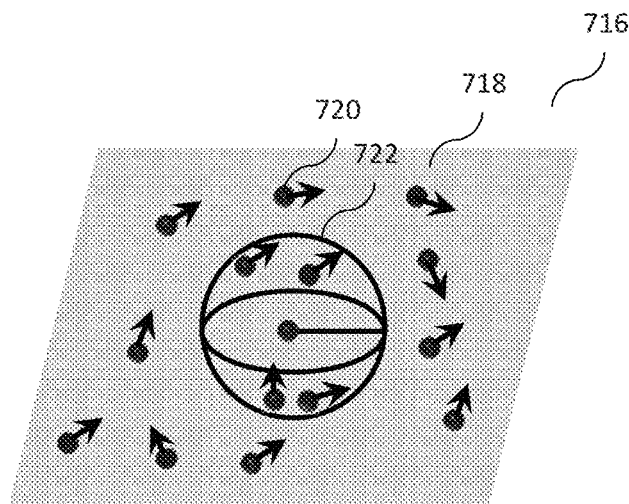
FIG. 7B depicts an illustration of destiny estimation based on conventional radiance estimation.
Figure 7C:
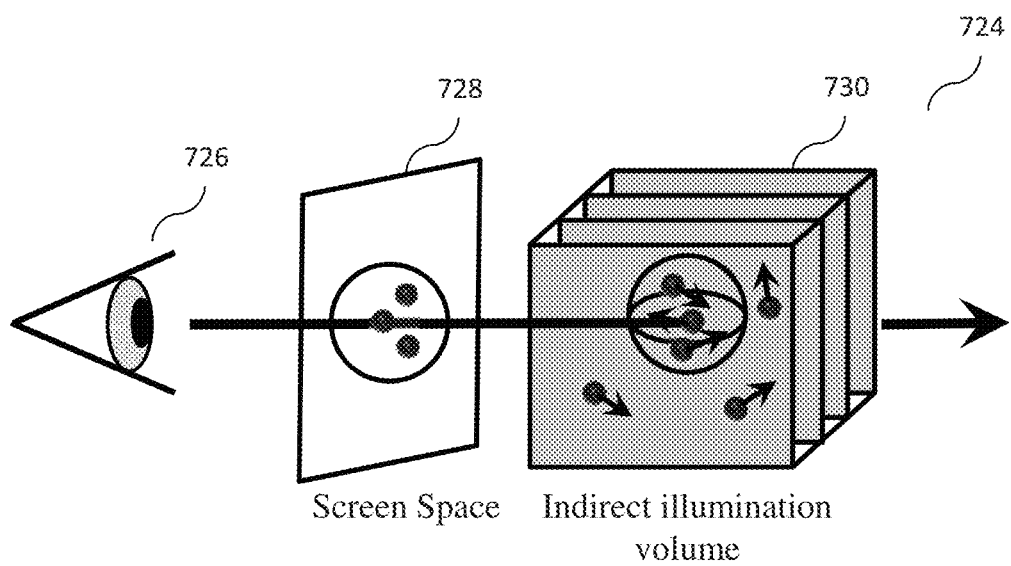
FIG. 7C depicts an illustration of estimation in screen space according to various embodiments.

FIG. 7B depicts an illustration 716 of destiny estimation based on conventional radiance estimation. A photon map 718 may be used to estimate the in-scattered radiance of each sample point along the ray. The n closest photons (one of them is representatively labelled as 720) are used to estimate the radiance using a spherical kernel 722 of radius r. However, such a scheme is computationally intensive and cannot fulfill the requirement of real-time ultrasound visualization FIG. 7C depicts an illustration 724 of estimation in screen space according to various embodiments. According to various embodiments, based on the concept of photon splatting, which is a dual approach of destiny estimation, each photon is regarded as a little disc, which is projected on a surface and may cover other project points (which is illustrated by various planes of an indirect illumination volume 730). The value of each influenced point is calculated by the energy of the photon weighted by the kernel function. According to various embodiments, the multiple scattering radiance in the screen space 728 (observed by an observer 726) is calculated since the step of sampling in the ray-casting is quite small, and in this case the photon can also be seen sequentially and real-time rendering is achieved.

Figure 8:
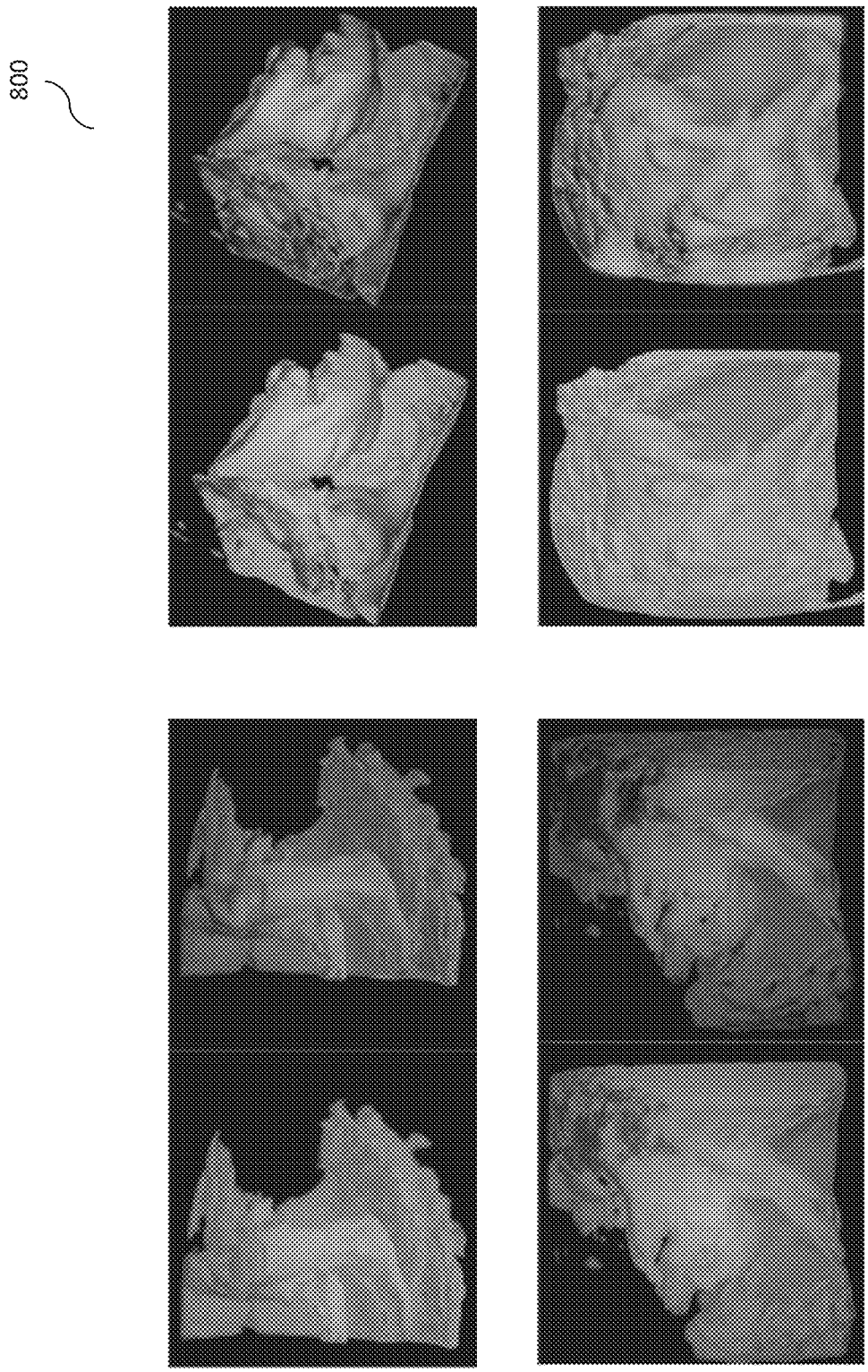
FIG. 8 depicts typical visualization results with different parameters according to various embodiments.

FIG. 8 depicts typical visualization results 800 with different parameters according to various embodiments.

Some portions of the description herein are explicitly or implicitly presented in terms of algorithms and functional or symbolic representations of operations on data within a computer memory. These algorithmic descriptions and functional or symbolic representations are the means used by those skilled in the data processing arts to convey most effectively the substance of their work to others skilled in the art. An algorithm is here, and generally, conceived to be a self-consistent sequence of steps leading to a desired result. The steps are those requiring physical manipulations of physical quantities, such as electrical, magnetic or optical signals capable of being stored, transferred, combined, compared, and otherwise manipulated.

Unless specifically stated otherwise, and as apparent from the description herein, it will be appreciated that throughout the present specification, discussions utilizing terms such as "receiving", "providing", "reducing", "determining", "generating", "outputting", or the like, refer to the action and processes of a computer system, or similar electronic device, that manipulates and transforms data represented as physical quantities within the computer system into other data similarly represented as physical quantities within the computer system or other information storage, transmission or display devices.

The present specification also discloses apparatus (or devices) for performing the operations of the methods. Such apparatus may be specially constructed for the required purposes, or may comprise a computer or other device selectively activated or reconfigured by a computer program stored in the computer. The algorithms and displays presented herein are not inherently related to any particular computer or other apparatus. Various machines may be used with programs in accordance with the teachings herein. Alternatively, the construction of more specialized apparatus to perform the required method steps may be appropriate. The structure of a computer suitable for executing the various methods/processes described herein will appear from the description herein.

In addition, the present specification also implicitly discloses a computer program, in that it would be apparent to the person skilled in the art that the individual steps of the method described herein may be put into effect by computer code. The computer program is not intended to be limited to any particular programming language and implementation thereof. It will be appreciated that a variety of programming languages and coding thereof may be used to implement the teachings of the disclosure contained herein. Moreover, the computer program is not intended to be limited to any particular control flow. There are many other variants of the computer program, which can use different control flows without departing from the spirit or scope of the invention.

Furthermore, one or more of the steps of the computer program may be performed in parallel rather than sequentially. Such a computer program may be stored on any computer readable medium. The computer readable medium may include storage devices such as magnetic or optical disks, memory chips, or other storage devices suitable for interfacing with a computer. The computer readable medium may also include a hard-wired medium such as exemplified in the Internet system, or wireless medium such as exemplified in the GSM mobile telephone system. The computer program when loaded and executed on such a computer effectively results in an apparatus that implements the steps of the preferred method.

According to various embodiments, a "module" or "circuit" may be understood as any kind of a logic implementing entity, which may be special purpose circuitry or a processor executing software stored in a memory, firmware, or any combination thereof. Thus, in an embodiment, a "module" may be a hard-wired logic circuit or a programmable logic circuit such as a programmable processor, e.g. a microprocessor (e.g. a Complex Instruction Set Computer (CISC) processor or a Reduced Instruction Set Computer (RISC) processor). A "module" may also be a processor executing software, e.g. any kind of computer program, e.g. a computer program using a virtual machine code such as e.g. Java. Any other kind of implementation of the respective functions which will be described in more detail below may also be understood as a "module" in accordance with an alternative embodiment.

From the above, it can be seen that the present embodiment provides ultrasound devices, ultrasound methods, and computer readable media for a high-fidelity and real-time 3D (fetal) ultrasound visualization system. In this regard, the ultrasound devices, ultrasound methods, and computer readable media include three key components: (1) an ultrasound denoising algorithm based on non-local self-similarity and phase information, (2) a clustering-based automated transfer function design scheme, and (3) a global illumination model for 3D ultrasound visualization based on volumetric photon mapping.

The ultrasound devices, ultrasound methods, and computer readable media according to various embodiments may advantageously remove speckle noise while simultaneously preserving important features in ultrasound data, which is important to achieve high-fidelity visualization results.

With the ultrasound devices, ultrasound methods, and computer readable media according to various embodiments, 3D ultrasound systems, for example 3D fetal ultrasound system, may be provided which more realistically visualize 3D (fetal) ultrasound data with more anatomical features in a real-time manner for diagnosis, so as to advantageously provide more cures or evidence for diagnosis in the visualization results.

The devices and methods according to various embodiments may be integrated in devices with an ultrasound sensor or connected to an ultrasound sensor, to provide more realistic visualization for fetal examination. The devices and methods may also be provided in a software system to be used in routine fetal examination by providing them more evidence for diagnosis.

While fetal ultrasound data has been described as exemplary ultrasound data in various embodiments, the devices and methods according to various embodiments may be used in visualizing any other high-dimensional ultrasound data, such as cardiac ultrasound data.

While exemplary embodiments have been presented in the foregoing detailed description of the invention, it should be appreciated that a vast number of variations exist. It should further be appreciated that the exemplary embodiments are only examples, and are not intended to limit the scope, applicability, operation, or configuration of the invention in any way. Rather, the foregoing detailed description will provide those skilled in the art with a convenient road map for implementing an exemplary embodiment of the invention, it being understood that various changes may be made in the function and arrangement of steps and method of operation described in the exemplary embodiment without departing from the scope of the invention as set forth in the appended claims.

What is claimed is:

1. An ultrasound device comprising:
   a sensor data receiver configured to receive ultrasound measurement data;
   a pre-processor configured to reduce noise of the ultrasound measurement data to obtain denoised data based on non-local self-similarity and phase information;
   a transfer function generator configured to generate a transfer function based on the denoised data; and
   a visualization circuit configured to generate a visualization of the ultrasound measurement data based on the transfer function and based on the denoised data.

2. The ultrasound device of claim 1,
   wherein the pre-processor is configured to estimate patch similarities of the ultrasound measurement data.

3. The ultrasound device of claim 2,
   wherein the pre-processor is configured to estimate the patch similarities based on integrating phase information of the ultrasound measurement data into a region covariance descriptor.

4. The ultrasound device of claim 2,
   wherein the pre-processor is configured to determine a patch group matrix based on the patch similarities.

5. The ultrasound device of claim 4,
   wherein the pre-processor is configured to determine a denoised matrix of lower rank corresponding to the patch group matrix.

6. The ultrasound device of claim 5,
   wherein the pre-processor is configured to determine the denoised matrix based on a singular value decomposition of the patch group matrix.

7. The ultrasound device of claim 1,
   wherein the visualization circuit is configured to use the transfer function to differentiate in the ultrasound measurement data between organs and tissues.

8. The ultrasound device of claim 1,
   wherein the transfer function generator is configured to determine the transfer function based on clustering of voxels obtained based on the ultrasound measurement data.

9. The ultrasound device of claim 1,
   wherein the visualization circuit is configured to generate the visualization based on volumetric photon mapping.

10. An ultrasound method comprising:
    receiving ultrasound measurement data;
    reducing noise of the ultrasound measurement data to obtain denoised data based on non-local self-similarity and phase information;
    generating a transfer function based on the denoised data; and
    generating a visualization of the ultrasound measurement data based on the transfer function and based on the denoised data.

11. The ultrasound method of claim 10,
    wherein reducing noise of the ultrasound measurement data based on non-local self-similarity and phase information comprises estimating patch similarities of the ultrasound measurement data.

12. The ultrasound method of claim 11,
    wherein the patch similarities are estimated based on integrating phase information of the ultrasound measurement data into a region covariance descriptor.

13. The ultrasound method of claim 11, further comprising:
    determining a patch group matrix based on the patch similarities.

14. The ultrasound method of claim 13, further comprising:
    determining a denoised matrix of lower rank corresponding to the patch group matrix.

15. The ultrasound method of claim 14,
    wherein the denoised matrix is determined based on a singular value decomposition of the patch group matrix.

16. The ultrasound method of claim 10,
    wherein generating the visualization comprises using the transfer function to differentiate in the ultrasound measurement data between organs and tissues.

17. The ultrasound method of claim 10,
    wherein the transfer function is determined based on clustering of voxels obtained based on the ultrasound measurement data.

18. The ultrasound method of claim 10,
    wherein the visualization is generated based on volumetric photon mapping.

19. A non-transitory computer readable medium having stored thereon executable instructions to have an ultrasound device perform an ultrasound method, the ultrasound method comprising:
    receiving ultrasound measurement data;
    reducing noise of the ultrasound measurement data to obtain denoised data based on non-local self-similarity and phase information;

generating a transfer function based on the denoised data; and generating a visualization of the ultrasound measurement data based on the transfer function and based on the denoised data.

* * * * *